(12) United States Patent
Malbin (10) Patent No.: US 12,408,852 B2
(45) Date of Patent: Sep. 9, 2025

(54) SYSTEM AND METHOD FOR PRIMING AN INTRAVENOUS LINE

(71) Applicant: Becton, Dickinson and Company, Franklin Lakes, NJ (US)

(72) Inventor: Alicia Malbin, Ridgewood, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 951 days.

(21) Appl. No.: 17/166,628

(22) Filed: Feb. 3, 2021

(65) Prior Publication Data
US 2021/0236031 A1    Aug. 5, 2021

Related U.S. Application Data

(60) Provisional application No. 62/970,226, filed on Feb. 5, 2020.

(51) Int. Cl.
*A61B 5/15* (2006.01)
*A61M 5/14* (2006.01)
*A61M 5/158* (2006.01)
*A61M 39/10* (2006.01)

(52) U.S. Cl.
CPC .. *A61B 5/150992* (2013.01); *A61B 5/150099* (2013.01); *A61M 5/1412* (2013.01); *A61M 5/1413* (2013.01); *A61M 5/158* (2013.01); *A61M 39/10* (2013.01); *A61M 2005/1402* (2013.01); *A61M 2039/1077* (2013.01)

(58) Field of Classification Search
CPC ....... A61B 5/150992; A61B 5/150099; A61M 5/1412; A61M 5/1413; A61M 5/158; A61M 39/10; A61M 2005/1402; A61M 2039/1077
See application file for complete search history.

(56) References Cited

U.S. PATENT DOCUMENTS

| | | | |
|---|---|---|---|
| 5,309,924 A * | 5/1994 | Peabody | A61B 5/150221 600/573 |
| 2006/0189925 A1* | 8/2006 | Gable | A61B 5/0086 600/316 |
| 2013/0317391 A1 | 11/2013 | Bullington et al. | |
| 2014/0014210 A1* | 1/2014 | Cederschiold | A61M 5/3286 53/381.2 |

(Continued)

FOREIGN PATENT DOCUMENTS

| | | |
|---|---|---|
| AU | 2018200901 A1 | 2/2018 |
| JP | 2017200534 A | 11/2017 |

*Primary Examiner* — Alex M Valvis
*Assistant Examiner* — Jonathan M Haney
(74) *Attorney, Agent, or Firm* — The Webb Law Firm (57) ABSTRACT

A system for priming an intravenous line includes a closed system transfer device having a first connector and a second connector, a connector device having a first connector and a second connector, a collection device having a first connector, a cannula having a distal end, and a sleeve having a first position where the distal end of the cannula is positioned within the sleeve and a second position where the distal end of the cannula is positioned outside of the sleeve, and at least one collection container having a closure. The collection container defines a volume having a negative pressure, with the cannula of the collection device configured to pierce the closure of the collection container.

17 Claims, 9 Drawing Sheets

(56) References Cited

U.S. PATENT DOCUMENTS

| | | | |
|---|---|---|---|
| 2014/0309553 A1* | 10/2014 | Spatafore | A61B 5/150755 600/576 |
| 2015/0119663 A1* | 4/2015 | Lim | A61B 5/1427 600/309 |
| 2015/0246352 A1* | 9/2015 | Bullington | A61B 50/33 422/546 |
| 2018/0193227 A1* | 7/2018 | Marici | A61M 5/1413 |

* cited by examiner

SYSTEM AND METHOD FOR PRIMING AN INTRAVENOUS LINE

CROSS-REFERENCE TO RELATED APPLICATION

The present application claims priority to U.S. Provisional Application Ser. No. 62/970,226, entitled "System and Method for Priming an Intravenous Line", filed Feb. 5, 2020, the entire disclosure of which is hereby incorporated by reference in its entirety.

BACKGROUND OF THE INVENTION

Field of the Disclosure

The present application relates generally to a system and method for priming an intravenous line.

Description of the Related Art

Health care providers reconstituting, transporting, and administering hazardous drugs, such as chemotherapeutic drugs, can put health care providers at risk of exposure to these medications and present a major hazard in the health care environment. For example, health care providers treating cancer patients risk being exposed to chemotherapy drugs and their toxic effects. Unintentional chemotherapy exposure can affect the nervous system, impair the reproductive system, and bring an increased risk of developing blood cancers in the future. In order to reduce the risk of health care providers being exposed to toxic drugs, the closed transfer of these drugs becomes important.

After connecting an intravenous line to an infusion container containing a hazardous drug using a connector, such as an IV bag spike, the intravenous line needs to be primed prior to infusion of the medicament within the infusion container into a patient. The intravenous line may be pre-primed using saline or other appropriate fluid. However, in cases where priming with a hazardous drug in line is desired, the hazardous drug is pushed through the intravenous line to remove the air with any fluid from the line being caught by a receptacle, such as a trash receptacle. Releasing hazardous drugs into an unsealed receptacle presents risks to health care providers and patients.

SUMMARY OF THE INVENTION

In one aspect or embodiment, a system for priming an intravenous line includes a closed system transfer device having a first connector and a second connector, with the first connector of the closed system transfer device configured to be connected to a connector of an intravenous line, a connector device having a first connector and a second connector, with the first connector of the connector device configured to be connected to the second connector of the closed system transfer device, a collection device having a first connector, a cannula having a distal end, and a sleeve having a first position where the distal end of the cannula is positioned within the sleeve and a second position where the distal end of the cannula is positioned outside of the sleeve. The first connector of the collection device is configured to be connected to the second connector of the connector device. The system also includes at least one collection container having a closure, with the collection container defining a volume having a negative pressure. The cannula of the collection device is configured to pierce the closure of the collection container.

The closed system transfer device may be a syringe adapter. The connector device may be a patient connector. The closed system transfer device may be a closeable male luer adapter. The connector device may be a needle-free connector. The collection device may be a blood collection device, and the at least one collection container may be a blood collection tube.

The closed system transfer device, the connector device, the collection device, and the at least one collection container may be configured to facilitate transfer of fluid from an intravenous line through the closed system transfer device, the connector device, the collection device, and into the at least one collection container without leaking of the fluid outside of the system.

The second connector of the closed system transfer device may include a membrane, and the first connector of the connector device may include a membrane, with the membrane of the second connector of the closed system transfer device configured to engage the membrane of the first connector of the connector device.

In a further aspect or embodiment of the present invention, a method of priming an intravenous line includes the steps of providing an intravenous line and a closed system transfer device comprising a first connector and a second connector, and connecting the closed system transfer device to the intravenous line. The method also includes the steps of providing a connector device comprising a first connector and a second connector, providing a collection device comprising a first connector, a cannula having a distal end, and a sleeve having a first position where the distal end of the cannula is positioned within the sleeve, and a second position where the distal end of the cannula is positioned outside of the sleeve, and connecting the connector device to the collection device. The method further includes the steps of connecting the closed system transfer device to the connector device, providing a collection container comprising a closure, the collection container defining a volume having a negative pressure, and priming the intravenous line by inserting the at least one collection container into the collection device such that the cannula of the collection device pierces the closure of the collection container.

The first connector of the connector device may be configured to be connected to the second connector of the closed system transfer device, and the first connector of the collection device may be configured to be connected to the second connector of the connector device.

In certain configurations, the method may also include the step of disconnecting the collection device and the connector device from the closed system transfer device.

The closed system transfer device may include a syringe adapter, and the connector device may include a patient connector. Optionally, the closed system transfer device may include a closeable male luer adapter, and the connector device may include a needle-free connector. In further configurations, the collection device may include a blood collection device, and the at least one collection container may be a blood collection tube.

BRIEF DESCRIPTION OF THE DRAWINGS

The above-mentioned and other features and advantages of this disclosure, and the manner of attaining them, will become more apparent and the disclosure itself will be better understood by reference to the following descriptions of aspects of the disclosure taken in conjunction with the accompanying drawings, wherein.

Corresponding reference characters indicate corresponding parts throughout the several views. The exemplifications set out herein illustrate exemplary aspects of the disclosure, and such exemplifications are not to be construed as limiting the scope of the disclosure in any manner.

DETAILED DESCRIPTION

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary aspects of the invention. Hence, specific dimensions and other physical characteristics related to the aspects disclosed herein are not to be considered as limiting. All numbers and ranges used in the specification and claims are to be understood as being modified in all instances by the term "about". By "about" is meant plus or minus twenty-five percent of the stated value, such as plus or minus ten percent of the stated value. However, this should not be considered as limiting to any analysis of the values under the doctrine of equivalents.

The terms "first", "second", and the like are not intended to refer to any particular order or chronology, but refer to different conditions, properties, or elements.

Referring to FIGS. 1-12, in one aspect or embodiment, a system 10 for priming an intravenous line 12 includes a closed system transfer device 14, a connector device 16, a collection device 18, and a collection container 20. The closed system transfer device 14 has a first connector 22 and a second connector 24, with the first connector 22 of the closed system transfer device 14 configured to be connected to a connector 26, such as a male luer connector, of the intravenous line 12. The intravenous line 12 may be connected to an infusion container 28, such as an IV bag, via a bag spike 30 or other suitable arrangement. The connector device 16 has a first connector 32 and a second connector 34, with the first connector 32 of the connector device 16 configured to be connected to the second connector 24 of the closed system transfer device 14. The collection device 18 has a first connector 36, a cannula 38 having a distal end 40, and a sleeve 42 having a first position where the distal end 40 of the cannula 38 is positioned within the sleeve 42 and a second position where the distal end 40 of the cannula 38 is positioned outside of the sleeve 42. More specifically, the sleeve 42 is configured to be compressed when the collection container 20 is inserted into the collection device 18 to move the sleeve 42 from the first position to the second position. When the collection container 20 is removed, the sleeve 42 is configured to return to the first position to seal the cannula 38 of the collection device 18. The first connector 36 of the collection device 18 is configured to be connected to the second connector 34 of the connector device 16. The collection container 20 includes a closure 44, with the collection container 20 defining a volume 46 having a negative pressure. The cannula 38 of the collection device 18 is configured to pierce the closure 44 of the collection container 20. Although one collection container 20 is shown, the system 10 may include one or more collection containers 20. In one embodiment or aspect, the first connector 22 of the closed system transfer device 14 is a female luer lock configured to be connected to a male luer connector 26 on the intravenous line 12.

As discussed in more detail below, the closed system transfer device 14, the connector device 16, the collection device 18, and the at least one collection container 20 are configured to facilitate transfer of fluid from the intravenous line 12 through the closed system transfer device 14, the connector device 16, the collection device 18, and into the at least one collection container 20 without leaking of the fluid outside of the system 10.

Figure 1:
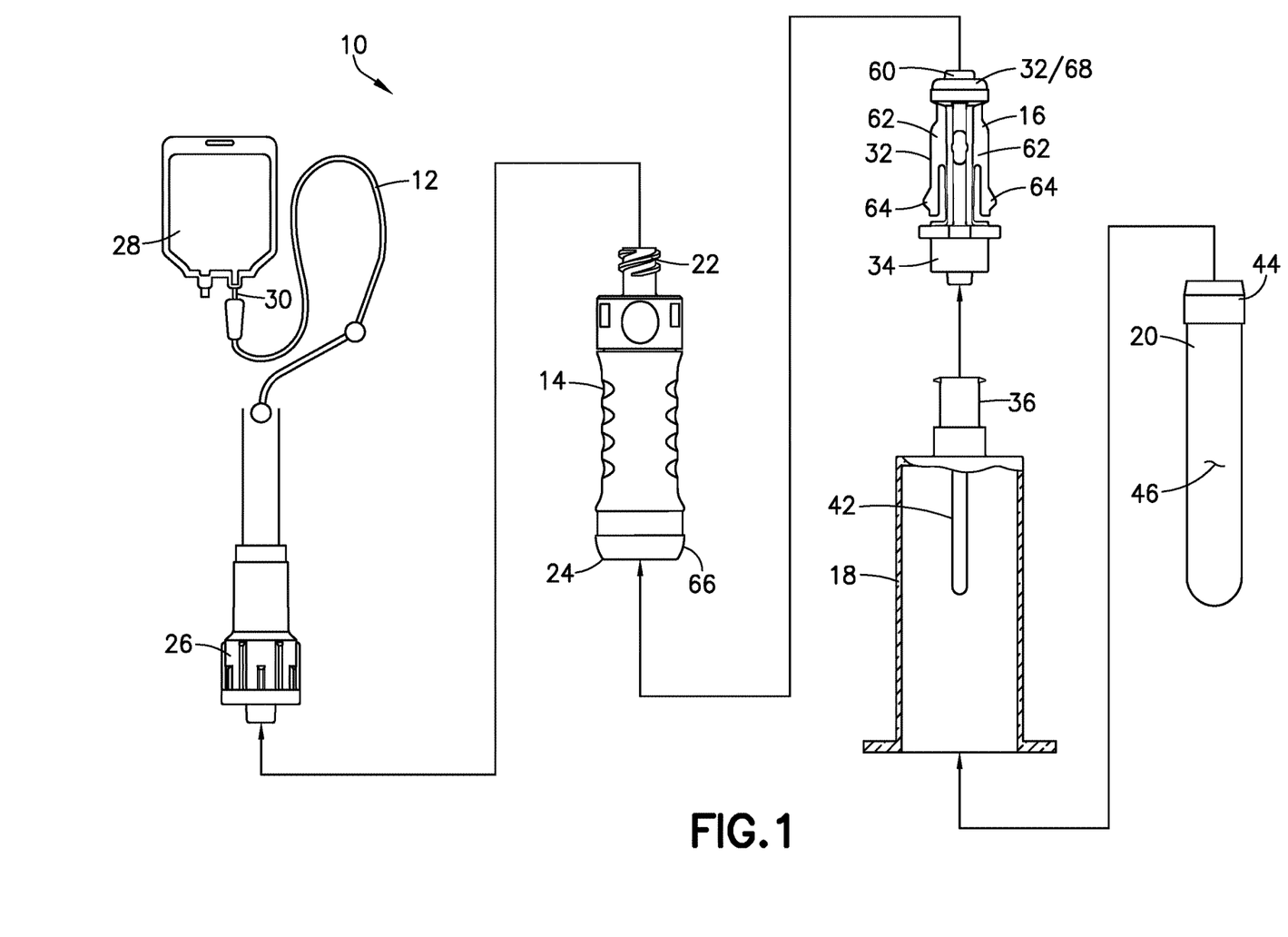
FIG. 1 is front view of a system for priming an intravenous line according to one aspect or embodiment of the present application.
Figure 2:
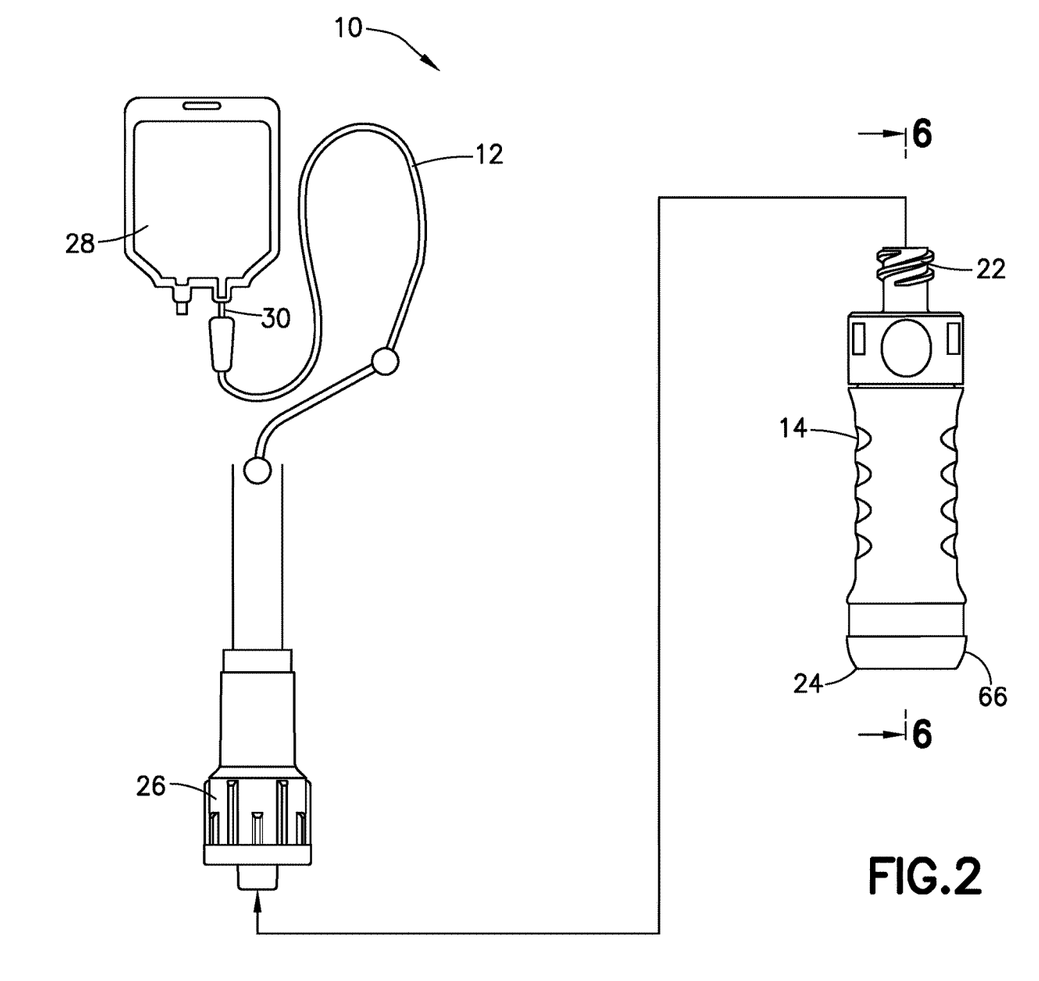
FIG. 2 is a front view of the system of FIG. 1, showing a closed system transfer device being connected to an intravenous line.
Figure 6:
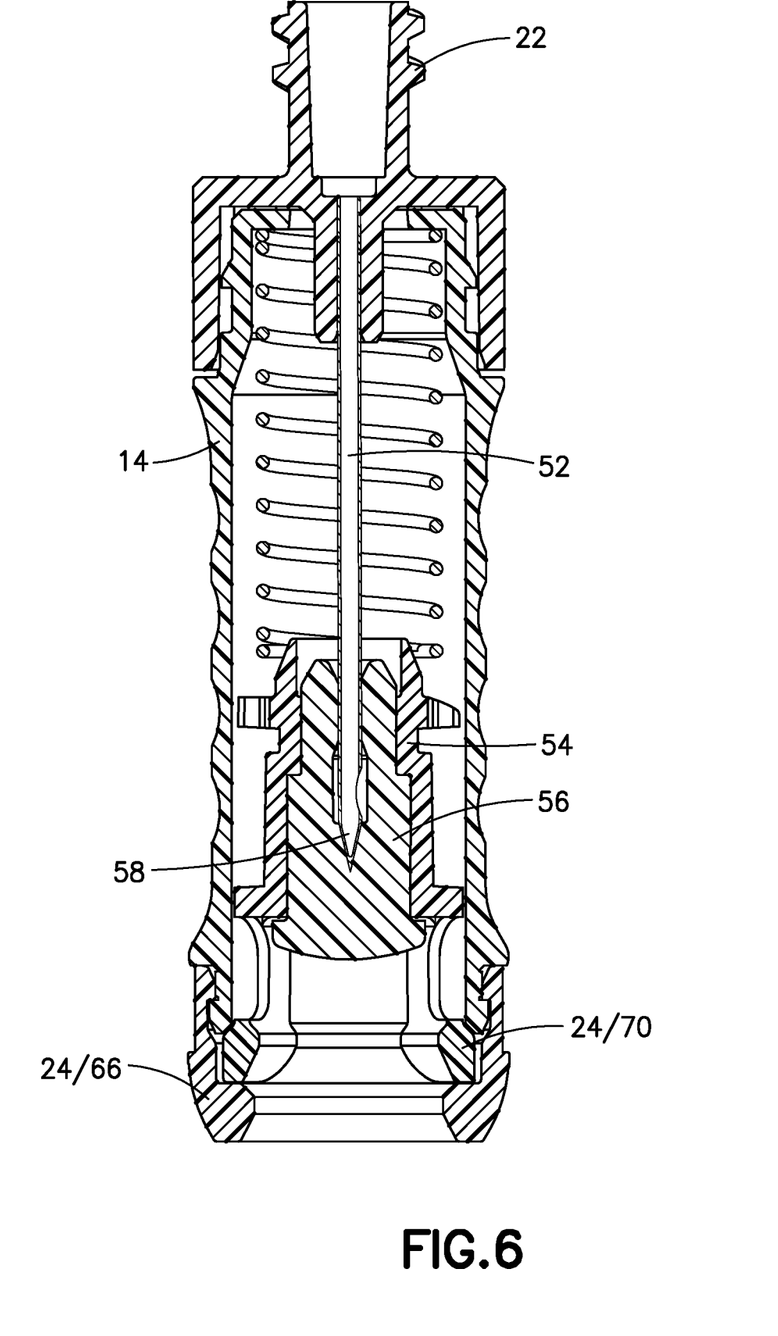
FIG. 6 is a cross-sectional view taken along line 6-6 in FIG. 2.

Referring to FIGS. 2 and 6, in one embodiment or aspect, the closed system transfer device 14 is a syringe adapter having a cannula 52 and a seal arrangement 54 with a membrane 56. The seal arrangement 54 is configured to move within the closed system transfer device 14 from a sealed position where a distal end 58 of the cannula 52 is sealed by the membrane 56 and a transfer position (not shown) where the distal end 58 of the cannula 52 extends through the membrane 56 to allow the cannula 52 to be placed in fluid communication with a mating connector, such as the connector device 16. When the connector device 16 is inserted into the closed system transfer device 14, the seal arrangement 54 is moved to the transfer position to place the cannula 52 in fluid communication with the connector device 16.

Figure 3:
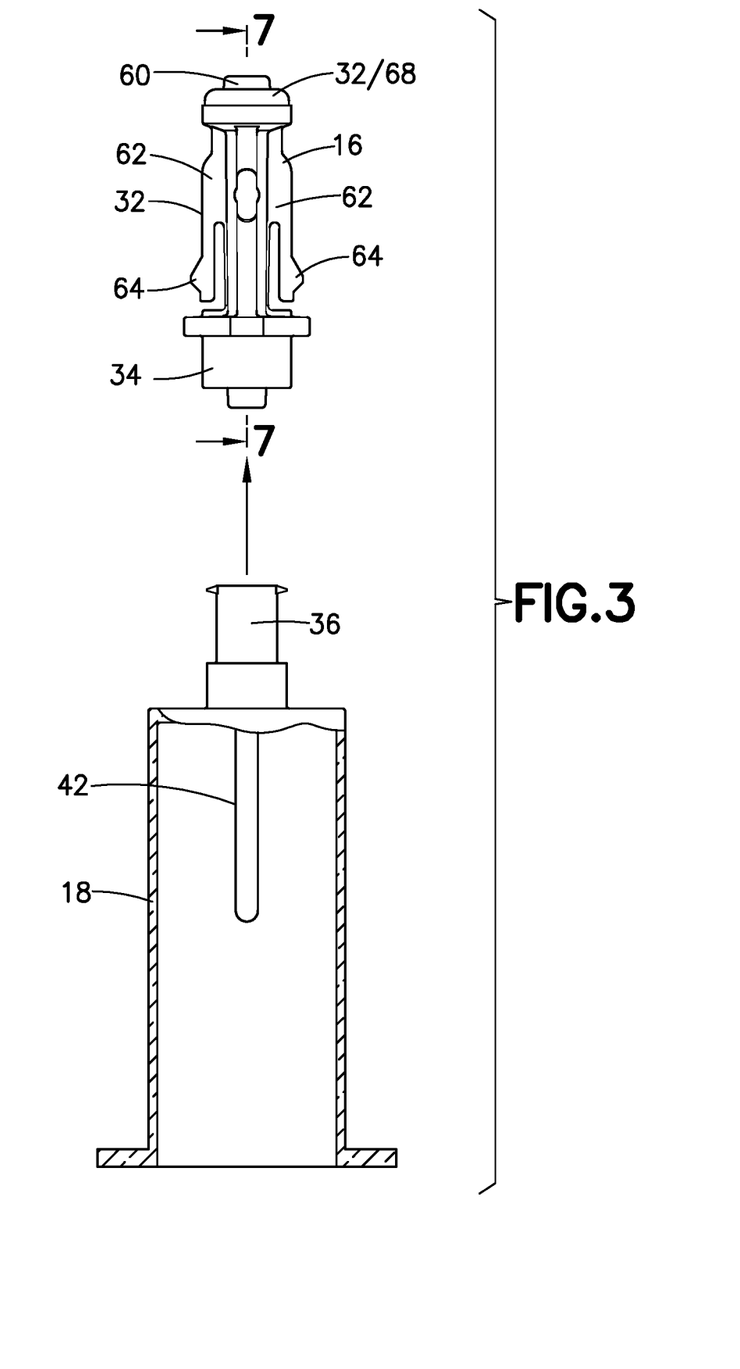
FIG. 3 is a front view of the system of FIG. 1, showing a connector being secured to a transfer device.
Figure 7:
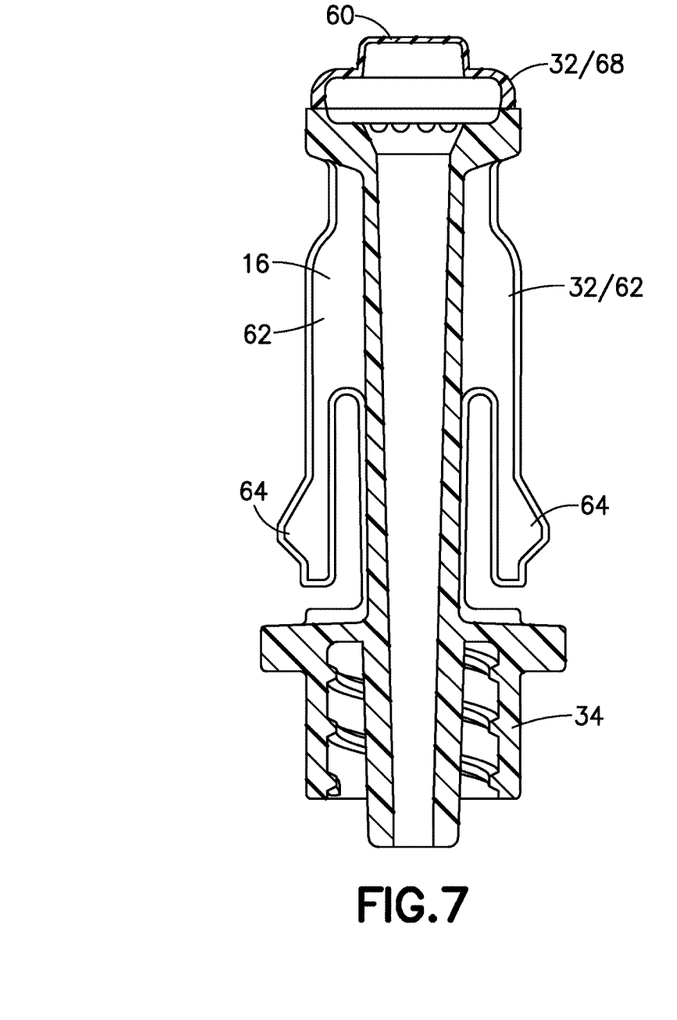
FIG. 7 is a cross-sectional view taken along line 7-7 in FIG. 3.

Referring to FIGS. 3 and 7, in one embodiment or aspect, the connector device 16 is a patient connector having a membrane 60 configured to engage the membrane 56 of the seal arrangement 54 of the closed system transfer device 14 when the connector device 16 is inserted into the closed system transfer device 14. The first connector 32 of the connector device 16 includes a pair of arms 62 with projections 64 configured to engage the second connector 24 of the closed system transfer device 14, which may be a portion of a housing 66 of the closed system transfer device 14. Alternatively, or in addition to, the first connector 32 of the connector device 16 includes a proximal portion 68 of the connector device 16, which engages a collet 70 of the closed system transfer device 14.

Figure 9:
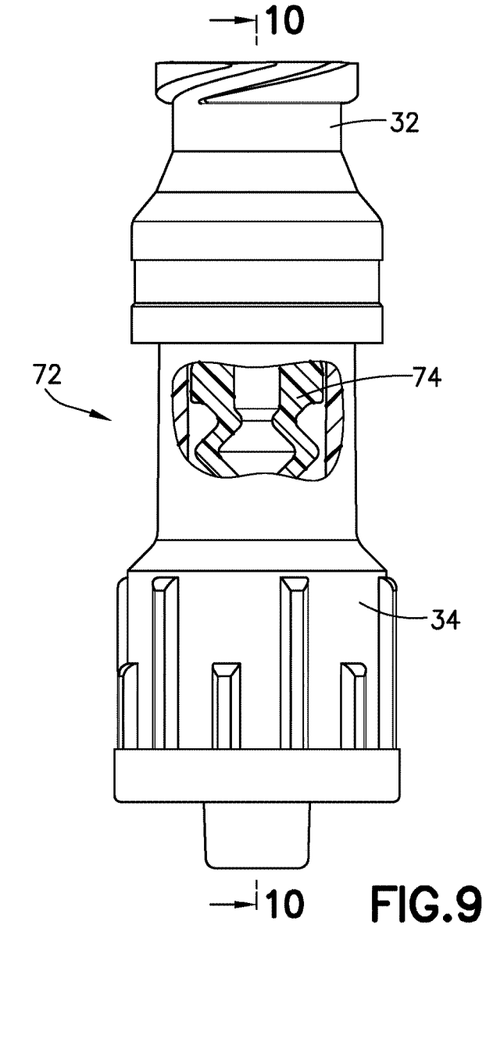
FIG. 9 is a front view of a connector according to a further aspect or embodiment of the present application.
Figure 10:
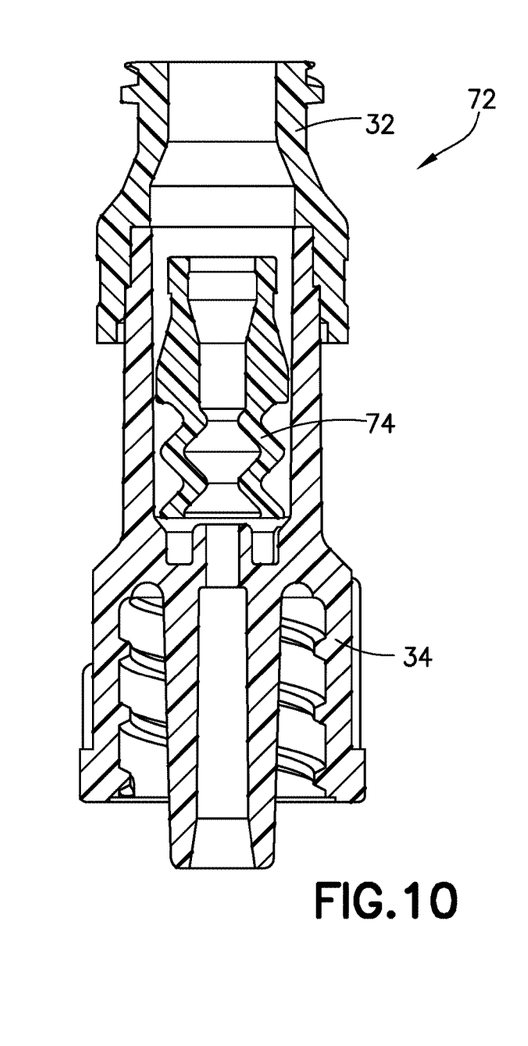
FIG. 10 is a cross-sectional view taken along line 10-10 in FIG. 9.

Referring to FIGS. 9 and 10, in a further embodiment or aspect, the connector device 16 is a needle-free connector 72 having an elastomeric sleeve 74, with the first connector 32 being a female luer connection and the second connector 34 being a male luer connection. The needle-free connector 72 may be the SmartSite™ available from Becton, Dickinson and Company, although other suitable needle-free connectors may be utilized.

Figure 11:
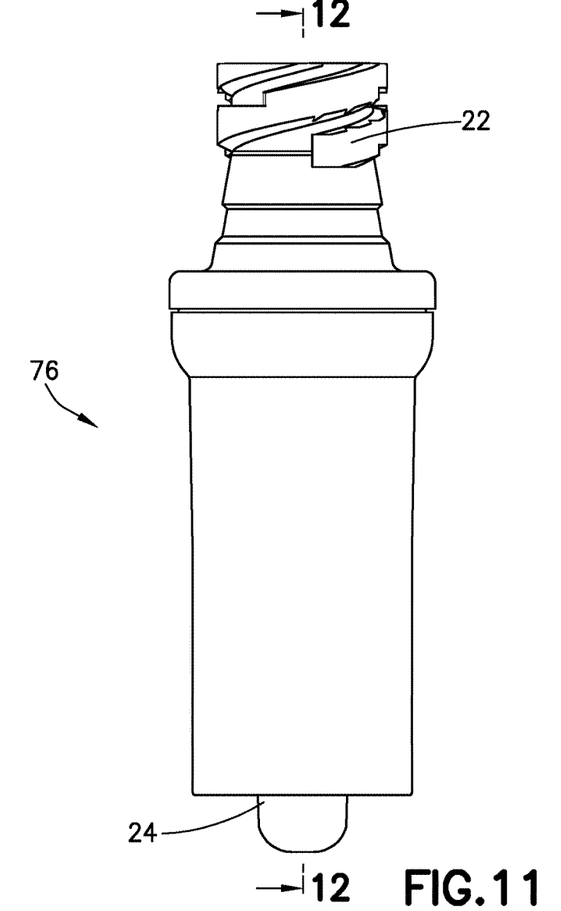
FIG. 11 is a front view of a closed system transfer device according to a further aspect or embodiment of the present application.
Figure 12:
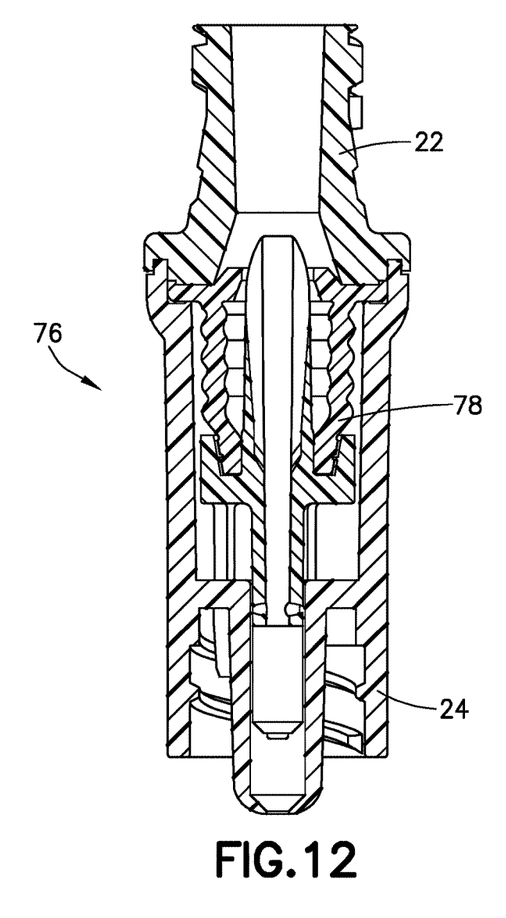
FIG. 12 is a cross-sectional view taken along line 12-12 in FIG. 11.

Referring to FIGS. 11 and 12, in a further embodiment or aspect, the closed system transfer device 14 is a closed male luer 76 having a valve arrangement 78. The first connector 22 is a female luer connection and the second connector 24 is a male luer connector configured to cooperate with the needle-free connector 72 of FIGS. 9 and 10. The closed male luer 76 may be the Texium™ closed male luer available from Becton, Dickinson and Company, although other suitable closed male luers may be utilized.

In one embodiment or aspect, the closed system transfer device 14 is formed integrally, bonded, or adhered to the intravenous line 12 or the male luer connector 26 of the intravenous line 12. In one embodiment or aspect, the connector device 16 is formed integrally, bonded, or adhered to the collection device 18.

Figure 8:
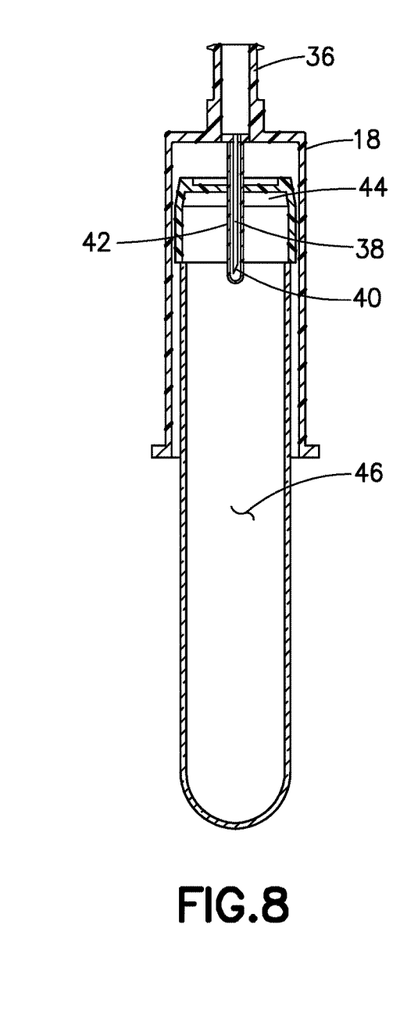
FIG. 8 is a cross-sectional view taken of the collection tube and transfer device shown in FIG. 4.

Referring to FIG. 8, in one embodiment or aspect, the collection device 18 is a blood collection device and the collection container 20 is a blood collection tube, such as the BD Vacutainer® blood collection tube, although other suitable collection devices or collection containers may be utilized.

Figure 4:
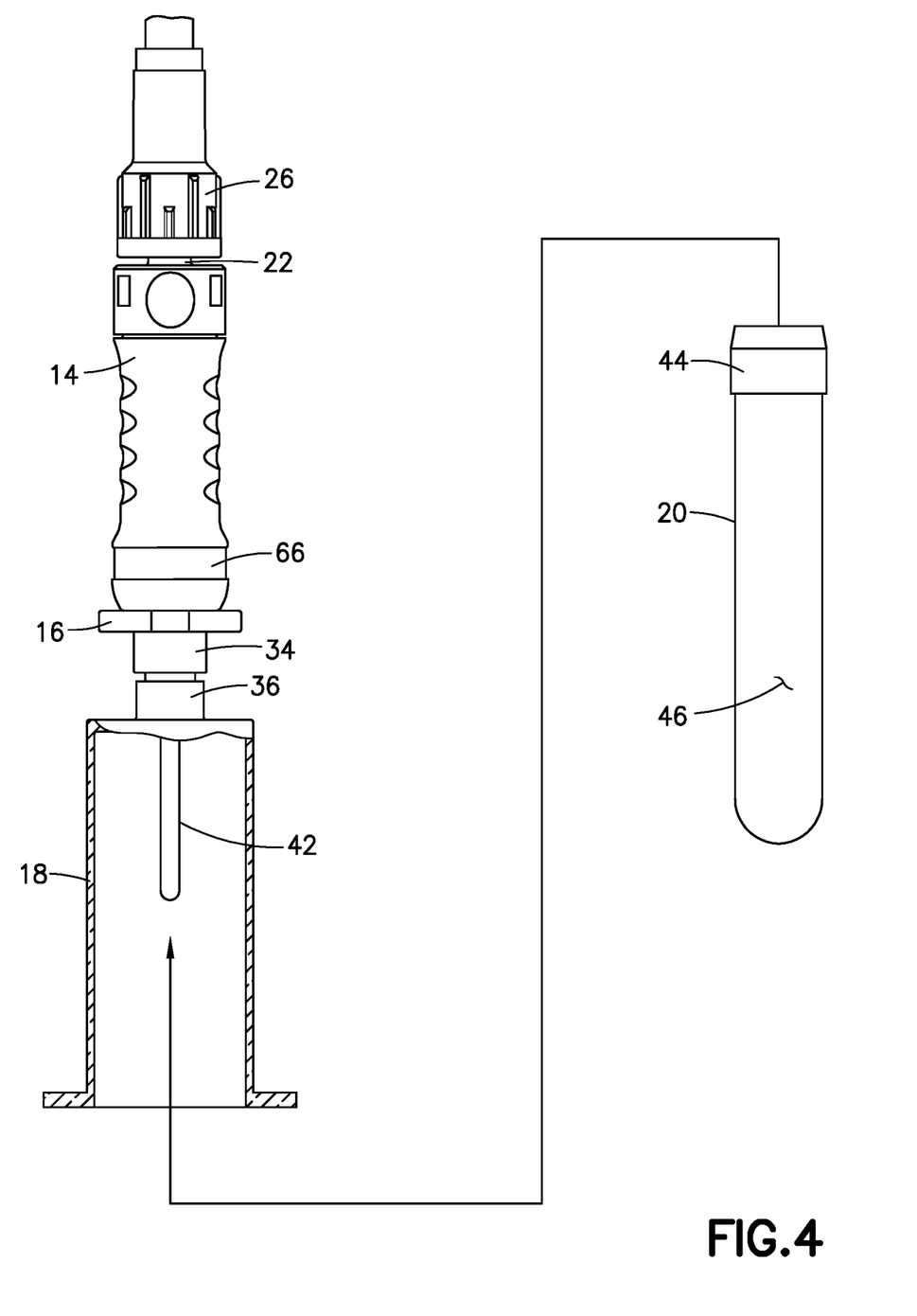
FIG. 4 is a front view of the system of FIG. 1, showing a collection tube inserted into the transfer device.
Figure 5:
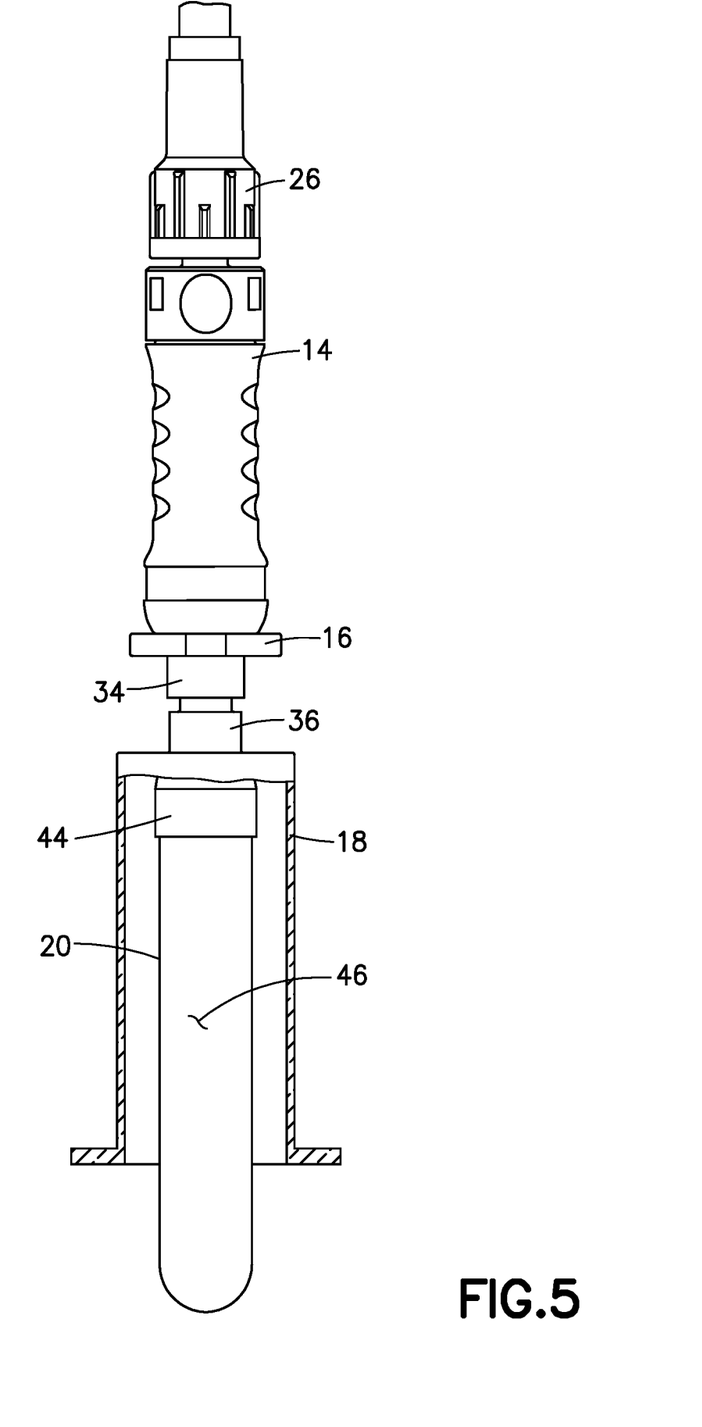
FIG. 5 is a front view of the system of FIG. 1, showing components of the system connected to each other.

Referring to FIGS. 2-5, in one embodiment or aspect, a method of priming the intravenous line 12 using the system 10 includes: connecting the closed system transfer device 14 to the intravenous line 12 (FIG. 2); connecting the connector device 16 to the collection device 18 (FIG. 3); connecting the closed system transfer device 14 to the connector device 16 (FIG. 4); and priming the intravenous line 12 by inserting the at least one collection container 20 into the collection device 18 such that the cannula 38 of the collection device 18 pierces the closure 44 of the collection container 20 (FIGS. 4 and 5). The method may further include disconnecting the collection device 18 and the connector device 16 from the closed system transfer device 14.

The first connector 22 of the closed system transfer device 14 is connected to the male luer connection 26 of the intravenous line 12, the second connector 34 of the connector device 16 is secured to the first connector 36 of the collection device 18, and the second connector 24 of the closed system transfer device 14 is secured to the first connector 32 of the connector device 16. When the collection container 20 is inserted into the collection device 18, the collection container 20 moves the sleeve 42 from the first position to the second position with the cannula 38 piercing the closure 44 of the collection container 20 such that the cannula 38 is in fluid communication with the volume 46 having the negative pressure. The negative pressure of the collection container 20 draws air and/or fluid from the intravenous line 12, through the closed system transfer device 14, through the connector device 16, through the collection device 18 and the cannula 38 of the collection device 18, and into the collection container 20 thereby purging air from the intravenous line 12. After disconnecting the connector device 16 and the collection device 18 from the closed system transfer device 14, the closed system transfer device 14 may remain connected to the intravenous line 12 to facilitate infusion into a patient. The system 10 is configured to prime the intravenous line 12 while in line with hazardous drugs while preventing leaks and/or dripping from the system 10 and the intravenous line 12. Although one collection container 20 is shown, the priming of the intravenous line 12 and other components may require one or more collection containers 20 depending on the volume of the intravenous line 12 and other components as well as the volume 46 of the collection container 20.

While this disclosure has been described as having exemplary designs, the present disclosure can be further modified within the spirit and scope of this disclosure. This application is therefore intended to cover any variations, uses, or adaptations of the disclosure using its general principles. To the extent possible, one or more features of any embodiment or aspect can be combined with one or more features of any other embodiment or aspect. Further, this application is intended to cover such departures from the present disclosure as come within known or customary practice in the art to which this disclosure pertains and which fall within the limits of the appended claims.

What is claimed is:

1. A system for priming an intravenous line comprising:
   a closed system transfer device comprising a first connector, a second connector, and a cannula extending at least partially between the first connector and the second connector, the first connector of the closed system transfer device configured to be connected to a connector of an intravenous line;
   a connector device comprising a first connector and a second connector, the first connector of the connector device configured to be received within and connected to the second connector of the closed system transfer device;
   a collection device comprising a first connector, a cannula having a distal end, and a sleeve having a first position where the distal end of the cannula of the collection device is positioned within the sleeve and a second position where the distal end of the cannula of the collection device is positioned outside of the sleeve, the first connector of the collection device configured to be connected to the second connector of the connector device; and
   at least one collection container comprising a closure, the at least one collection container defining a volume having a negative pressure,
   wherein the cannula of the collection device is configured to pierce the closure of the collection container, and
   wherein the second connector of the closed system transfer device comprises a membrane,
   wherein, in a sealed position, a distal end of the cannula of the closed system transfer device is held at least partially within the membrane of the second connector of the closed system transfer device,
   wherein the first connector of the connector device comprises a membrane, the membrane of the second connector of the closed system transfer device configured to engage the membrane of the first connector of the connector device, and
   wherein, in a transfer position, the first connector of the connector device is received within the second connector of the closed system transfer device thereby causing the cannula of the closed system transfer device to extend through at least the membrane of the second connector of the closed system transfer device to establish fluid communication between the closed system transfer device and the connector device.

2. The system of claim 1, wherein the closed system transfer device comprises a syringe adapter.

3. The system of claim 2, wherein the connector device comprises a patient connector.

4. The system of claim 1, wherein the closed system transfer device comprises a closeable male luer adapter.

5. The system of claim 1, wherein the connector device comprises a needle-free connector.

6. The system of claim 1, wherein the collection device comprises a blood collection device, and wherein the at least one collection container comprises a blood collection tube.

7. The system of claim 1, wherein the closed system transfer device, the connector device, the collection device, and the at least one collection container are configured to facilitate transfer of fluid from the intravenous line through the closed system transfer device, the connector device, and the collection device, and into the at least one collection container.

8. The system of claim 7, wherein the closed system transfer device, the connector device, and the collection device are configured to transfer the fluid from the intravenous line into the at least one collection container without leaking.

9. A method of priming an intravenous line, the method comprising:
providing an intravenous line and a closed system transfer device comprising a first connector, a second connector, and a cannula extending at least partially between the first connector and the second connector;
connecting the closed system transfer device to the intravenous line;
providing a connector device comprising a first connector and a second connector;
providing a collection device comprising a first connector, a cannula having a distal end, and a sleeve having a first position where the distal end of the cannula is positioned within the sleeve, and a second position where the distal end of the cannula is positioned outside of the sleeve;
connecting the connector device to the collection device;
connecting the closed system transfer device to the connector device by securing the first connector of the connector device within the second connector of the closed system transfer device, thereby engaging a membrane of the second connector of the closed system transfer device with a membrane of the first connector of the connector device and causing the cannula of the closed system transfer device to extend through the membrane of the second connector of the closed system transfer device;
providing a collection container comprising a closure, the collection container defining a volume having a negative pressure; and
priming the intravenous line by inserting the collection container into the collection device such that the cannula of the collection device pierces the closure of the collection container.

10. The method of claim 9, wherein the first connector of the connector device is configured to be connected to the second connector of the closed system transfer device.

11. The method of claim 9, wherein the first connector of the collection device is configured to be connected to the second connector of the connector device.

12. The method of claim 9, further comprising:
disconnecting the collection device and the connector device from the closed system transfer device.

13. The method of claim 9, wherein the closed system transfer device comprises a syringe adapter.

14. The method of claim 13, wherein the connector device comprises a patient connector.

15. The method of claim 9, wherein the closed system transfer device comprises a closeable male luer adapter.

16. The method of claim 9, wherein the connector device comprises a needle-free connector.

17. The method of claim 9, wherein the collection device comprises a blood collection device, and wherein the collection container comprises a blood collection tube.

* * * * *